(12) United States Patent
Sahin et al.

(10) Patent No.: US 11,904,086 B2
(45) Date of Patent: Feb. 20, 2024

(54) ELECTRONIC DISPERSION DEVICE

(71) Applicant: Altria Client Services LLC, Richmond, VA (US)

(72) Inventors: Buket Sahin, Richmond, VA (US); Gerd Kobal, Sandy Hook, VA (US); Qiang Wang, Glen Allen, VA (US); Christopher S. Tucker, Midlothian, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 18/155,297

(22) Filed: Jan. 17, 2023

(65) Prior Publication Data

US 2023/0173199 A1 Jun. 8, 2023

Related U.S. Application Data

(63) Continuation of application No. 16/283,277, filed on Feb. 22, 2019, now Pat. No. 11,607,506.

(51) Int. Cl.
*A61M 11/00* (2006.01)
*A61M 11/04* (2006.01)
*A61M 16/00* (2006.01)

(52) U.S. Cl.
CPC ......... *A61M 11/005* (2013.01); *A61M 11/042* (2014.02); *A61M 16/0003* (2014.02); *A61M 2205/3375* (2013.01)

(58) Field of Classification Search
CPC .............. A61M 11/005; A61M 11/042; A61M 11/0003; A61M 2205/3375
USPC ........................................................ 131/329
See application file for complete search history.

(56) References Cited

U.S. PATENT DOCUMENTS

| | | | |
|---|---|---|---|
| 6,568,390 B2 | 5/2003 | Nichols et al. | |
| 7,173,222 B2 | 2/2007 | Cox et al. | |
| 7,540,286 B2 | 6/2009 | Cross et al. | |
| 8,550,069 B2 | 10/2013 | Alelov | |
| 8,915,254 B2 | 12/2014 | Monsees et al. | |
| 9,072,321 B2 | 7/2015 | Liu | |
| 9,399,110 B2 | 7/2016 | Goodman et al. | |
| 9,675,117 B2 * | 6/2017 | Li | A24F 40/60 |
| 10,034,495 B2 | 7/2018 | Alarcon et al. | |
| 10,051,892 B2 | 8/2018 | Rogan et al. | |
| 10,368,581 B2 * | 8/2019 | Rostami | A61M 11/042 |

(Continued)

FOREIGN PATENT DOCUMENTS

| | | |
|---|---|---|
| CN | 201869778 U | 6/2011 |
| CN | 202445135 U | 9/2012 |

(Continued)

OTHER PUBLICATIONS https://www.youtube.com/watch?v=igIGRXZeYPs.
Building Blu, Title of Presentation: "Creating Something Better for the World's Smokers." 165 Pages.
OMRON Instruction Manual, U22 Micro A-I-R.
International Search Report and Written Opinion dated May 26, 2020.
Written Opinion dated Feb. 8, 2021.

(Continued)

*Primary Examiner* — Harshad C Patel
(74) *Attorney, Agent, or Firm* — Harness, Dickey & Pierce, P.L.C.

(57) ABSTRACT

A dispersion device includes a first dispersion generating system, a second dispersion generating system and an outlet end element including a first outlet corresponding to the first dispersion generating system and a second outlet corresponding to the second dispersion generating system.

20 Claims, 8 Drawing Sheets

(56) References Cited

U.S. PATENT DOCUMENTS

| | | |
|---|---|---|
| 10,834,969 B2 | 11/2020 | Godfrey et al. |
| 11,439,183 B2 * | 9/2022 | Woodcock ............ G08B 21/182 |
| 2014/0060527 A1 | 3/2014 | Liu |
| 2014/0060556 A1 | 3/2014 | Liu |
| 2014/0261488 A1 * | 9/2014 | Tucker .................... A24F 40/50 |
| | | 131/328 |
| 2014/0366898 A1 | 12/2014 | Monsees et al. |
| 2015/0020823 A1 | 1/2015 | Lipowicz et al. |
| 2015/0216236 A1 | 8/2015 | Bless et al. |
| 2015/0305410 A1 | 10/2015 | Liu |
| 2015/0313275 A1 | 11/2015 | Anderson et al. |
| 2016/0198771 A1 | 7/2016 | Goggin et al. |
| 2016/0331026 A1 | 11/2016 | Cameron |
| 2016/0334119 A1 * | 11/2016 | Cameron ................ A24F 40/30 |
| 2016/0353800 A1 | 12/2016 | Di Carlo |
| 2017/0251727 A1 * | 9/2017 | Nielsen ................... A24F 40/40 |
| 2017/0258138 A1 | 9/2017 | Rostami et al. |
| 2017/0258140 A1 | 9/2017 | Rostami et al. |
| 2017/0325502 A1 | 11/2017 | Nelson et al. |
| 2018/0017980 A1 * | 1/2018 | Halevi .................... F24F 6/025 |
| 2018/0213847 A1 | 8/2018 | Reevell |

FOREIGN PATENT DOCUMENTS

| | | |
|---|---|---|
| EP | 3170413 A1 | 5/2017 |
| RU | 2602962 C2 | 11/2016 |
| WO | WO-2019/030602 A1 | 2/2019 |

OTHER PUBLICATIONS

International Preliminary Report on Patentability dated May 14, 2021.

Russian Office Action and Search Report for Application No. 2021126957, dated Jun. 26, 2023, with English Translation.

Philippine Office Action for Application No. 1/2021/551228, dated Jul. 5, 2023, with English Translation.

Russian Notice of Allowance and English translation thereof dated Sep. 4, 2023.

Philippine Subsequent Substantive Examination Report dated Sep. 22, 2023.

Philippines Notice of Allowance for Philippines Application No. 1-2021-551228 dated Dec. 13, 2023.

* cited by examiner

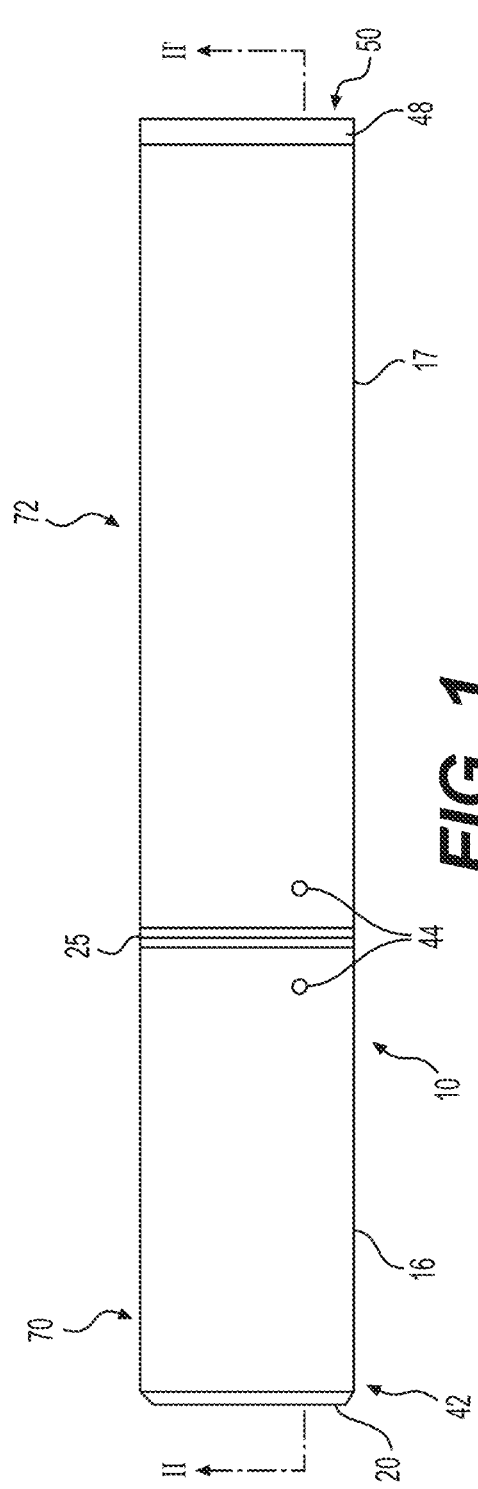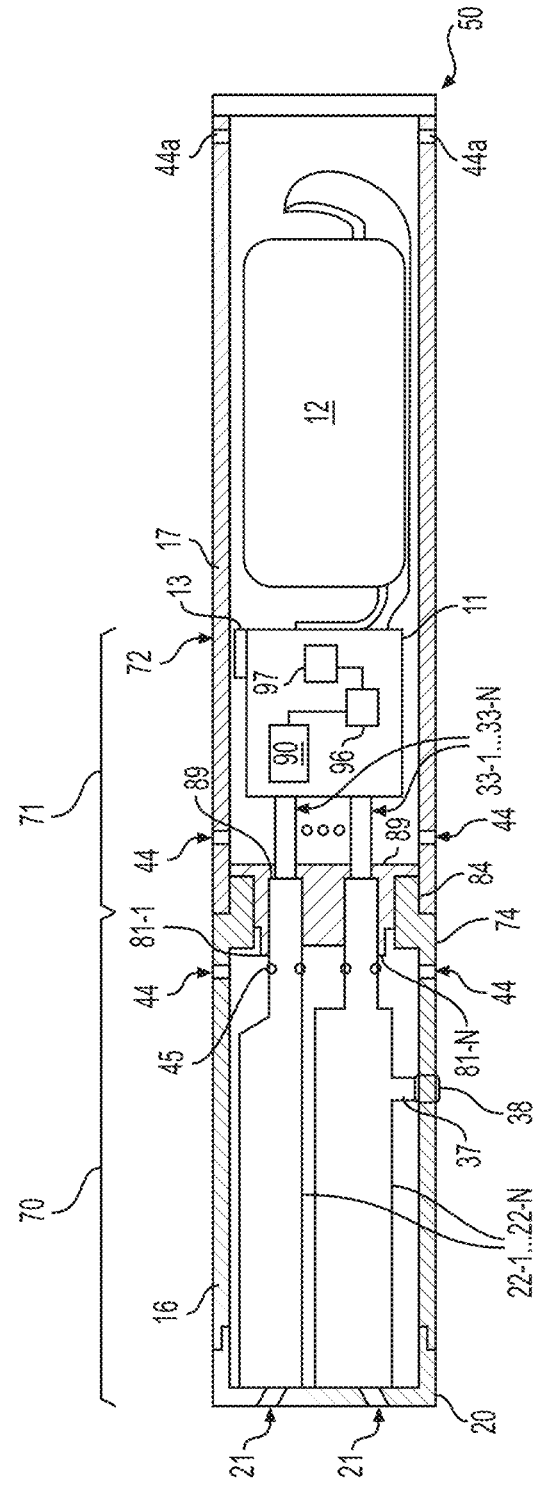

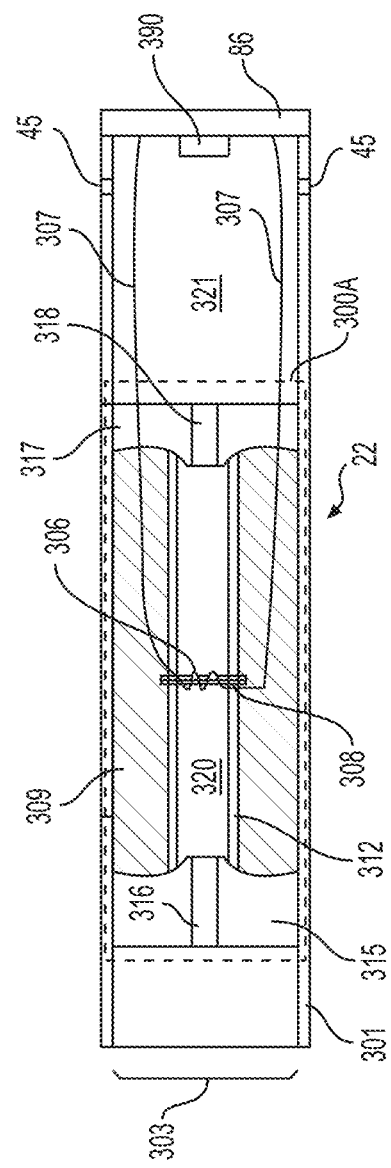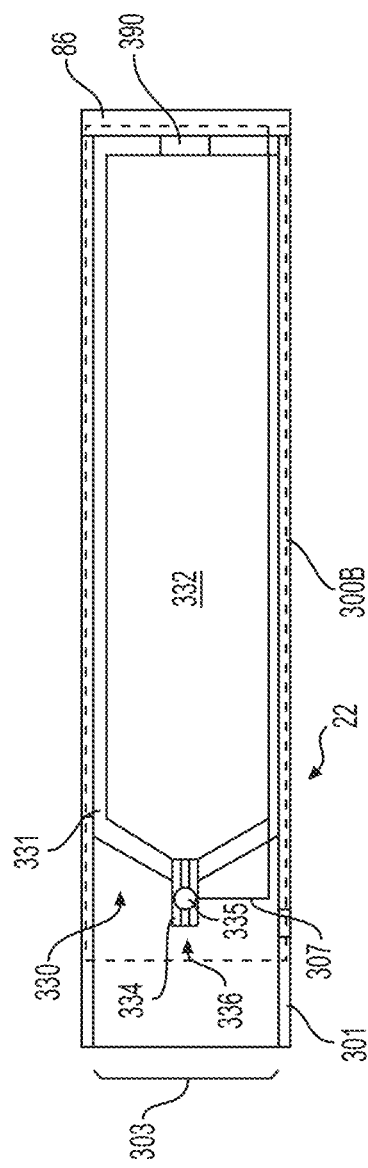

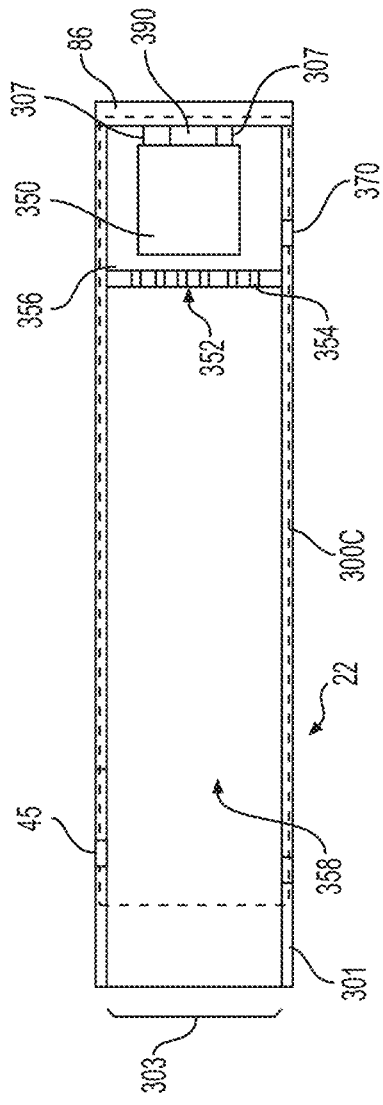
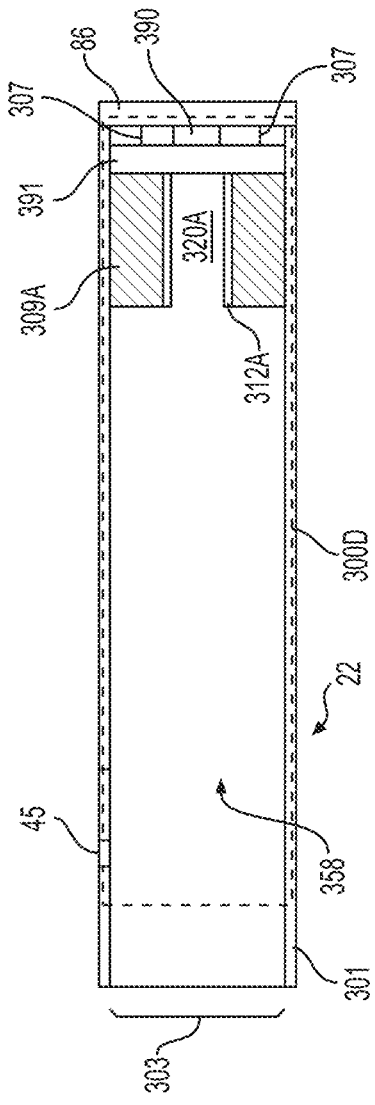

ELECTRONIC DISPERSION DEVICE

CROSS-REFERENCE TO RELATED APPLICATIONS

The present application is a Continuation of U.S. application Ser. No. 16/283,277, filed on Feb. 22, 2019, the entire contents are incorporated herein by reference.

BACKGROUND

Field

The present disclosure relates to an electronic dispersion device.

Description of Related Art

Dispersion devices include, for example, electronic vaping devices and aerosol generating devices. An electronic vaping or e-vaping device includes a heating element that vaporizes a pre-vapor formulation to produce a vapor.

An aerosol generating device may generate an aerosol without a heating element.

SUMMARY

Some example embodiments provide dispersion device including a first dispersion generating system, a second dispersion generating system and an outlet end element including a first outlet corresponding to the first dispersion generating system and a second outlet corresponding to the second dispersion generating system.

In some example embodiments, the device further includes a divider separating the first dispersion generating system and the first outlet from the second dispersion generating system and the second outlet.

In some example embodiments, the first dispersion generating system is configured to vaporize a first pre-vapor formulation into a first vapor having particles of a first size.

In some example embodiments, the second dispersion generating system is configured to aerosolize a first pre-aerosol formulation into a first aerosol having particles of a second size and the first size and the second size are different.

In some example embodiments, a first cartridge contains the first pre-vapor formulation and a second cartridge contains the first pre-aerosol formulation, the first pre-vapor formulation and the first pre-aerosol formulation being different.

In some example embodiments, the first dispersion generating system includes a heater and the second dispersion generating system includes a heatless vapor generator.

In some example embodiments, the first dispersion generating system includes a heater configured to generate the first vapor and the second dispersion generating system includes an ultra-sonic generator or a vibrator configured to generate the first aerosol.

In some example embodiments, the first outlet is at a center of the outlet end element.

In some example embodiments, the second outlet includes first and second parts at end portions of the outlet end element.

In some example embodiments, the device further includes a power supply coupled to the first dispersion generating system and the second dispersion generating system.

In some example embodiments, the device further includes an outer housing containing the first dispersion generating system and the second dispersion generating system and a divider defining first and second passages in the outer housing, the first dispersion generating system being in the first passage and the second dispersion generating system being in the second passage.

In some example embodiments, the divider extends to the outlet end element and separates the first outlet and the second outlet.

In some example embodiments, the housing defines a first opening through a surface of the housing, the first dispersion generating system defines a second opening, and the first opening and the second opening align.

In some example embodiments, the first dispersion generating system includes a sonicator configured to exert a force on a pre-aerosol formulation and a mesh plate adjacent to the pre-aerosol formulation, the mesh plate defining holes such that an aerosol exits the mesh plate when the sonicator exerts the force on the pre-aerosol formulation, the mesh plate separates the pre-aerosol formulation from a channel.

In some example embodiments, the second dispersion generating system includes a pre-aerosol formulation reservoir configured to contain a pre-aerosol formulation, an inner tube defining a central channel through the pre-vapor formulation reservoir and a vibrator configured to vibrate the pre-vapor formulation to generate a vapor.

In some example embodiments, the vibrator is a plate and contacts the pre-vapor formulation reservoir.

In some example embodiments, the inner tube extends from the plate to an end of the pre-vapor formulation reservoir.

In some example embodiments, the first outlet and the second outlet are angled with respect to a longitudinal axis of the e-vaping device.

In some example embodiments, the device further includes a first cartridge including the first dispersion generating system and a second cartridge including the second dispersion generation system, the first cartridge and the second cartridge contacting the outlet end element.

In some example embodiments, each of the first cartridge and the second cartridge includes an air inlet.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1 is a side view of an electronic device according to some example embodiments.

FIG. 2 is a cross-sectional view the electronic device shown in FIG. 1 along line II-II' according to some example embodiments.

FIG. 3 is a cross-sectional view of an example embodiment of the electronic device shown in FIG. 1 along line II-II'.

FIG. 4 is a perspective view of a cartridge holder according to some example embodiments.

FIGS. 5A-5D are cartridges that include dispersion generators according to some example embodiments.

FIGS. 6A-6D illustrate example embodiments of an outlet end insert.

Figure 7A:
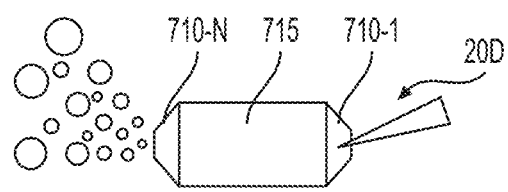
Figure 7B:
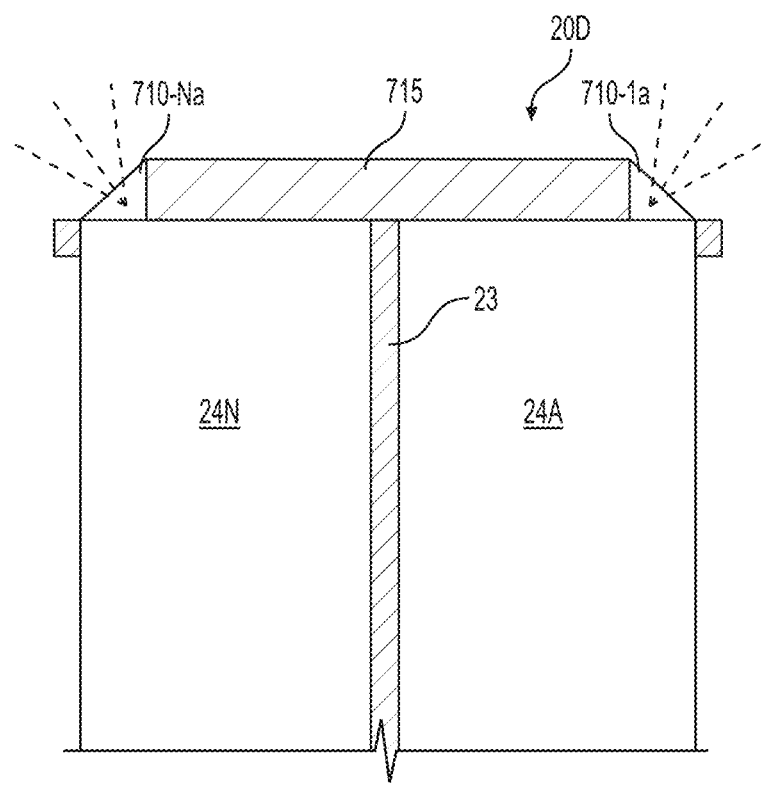

FIGS. 7A-7B an outlet end insert according to some example embodiments.

DETAILED DESCRIPTION

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, or the like, may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a side view of an e-vaping device according to at least one example embodiment. FIG. 2 is a cross-sectional view of the device 10 along line II-II in FIG. 1.

Referring to FIG. 1 and FIG. 2, a device 10 may include a cover (or first section) 70, a reusable base (or second section) 71 and one or more cartridges 22-1 to 22-N, where "N" is a positive integer.

The base 71 includes a power supply section 72 and a cartridge holder 80 in an outer housing 17. The cartridge holder 80 is coupled to the power supply section 72. The cover 70 and base 71 are coupled together at complimentary interfaces 74, 84. In some example embodiments, interface 84 is included in the cartridge holder 80, and the cover 70 and cartridge holder 80 may be coupled together via interfaces 74, 84. In some example embodiments, interface 84 is included in the power supply section 72, and the cover 70 and power supply section 72 may be coupled together via interfaces 74, 84.

In some example embodiments, the interfaces 74, 84 are threaded connectors. It should be appreciated that an interface 74, 84 may be any type of connector, including, without limitation, a snug-fit, detent, clamp, bayonet, sliding fit, sleeve fit, alignment fit, magnetic, clasp, or any other type of connection, and/or combinations thereof.

In at least one example embodiment, the interfaces 74, 84 may be a connector as described in U.S. application Ser. No. 15/154,439, filed May 13, 2016, the entire contents of which are incorporated herein by reference thereto. As described in U.S. application Ser. No. 15/154,439, the interfaces 74, 84 may be formed by a deep drawn process.

The outer housing 17 extends in a longitudinal direction. The outer housing 17 may have a generally cylindrical cross-section. In some example embodiments, the outer housing 17 may have a generally triangular cross-section, a generally rectangular cross-section, a generally oval cross-section, a generally square cross-section, a generally polygonal cross-section, or any other suitable cross-section shape. In some example embodiments, the outer housing 17 may have a greater circumference or dimensions at a second end 50 than at an end near the interface 84.

In other example embodiments, the outer housing 17 may have a generally rectangular, oval, square, or polygonal cross-section, or any other suitable cross-section shape along the base 71.

The device 10 includes an outlet end (e.g., a mouth end) insert 20 at a first end 42, and an end cap 48 at the second end 50.

Although example embodiments may be described in some instances with regard to the cover 70 coupled to the base 71, example embodiments should not be limited to these examples.

As shown in FIG. 2, the device 10 includes two cartridges. Thus, in some example embodiments, "N" has a value of at least two (2). The cover 70 and base 71 may be part of an e-vaping device kit. An e-vaping device kit may be a package that may include at least one cartridge 22-1 to 22-N, a cover 70, a base 71, and a power supply charger configured to couple with the base 71 and supply electrical power to a power supply 12 included therein. As shown in FIG. 2, the base 71 is configured to couple with one or more cartridges 22-1 to 22-N to support vaping. In some example embodiments, a base for an e-vaping device includes the base 71 and excludes the cover 70.

Referring to FIG. 1 and FIG. 2, the device 10 includes multiple separate cartridges 22-1 to 22-N. As used herein, "N" is a positive integer having a value of at least one (1). In some example embodiments, "N" has a value of at least two (2), such that the base 71 is configured to couple with at least two cartridges 22-1 to 22-N. Cartridges 22-1 to 22-N are described in further detail below with regard to FIGS. 5A-5D.

In some example embodiments, each separate cartridge of cartridges 22-1 to 22-N includes one or more dispersion generators. In the example embodiment shown in FIG. 2, the separate cartridges 22-1 to 22-N include separate ones of at least first and second dispersion generators such that cartridge 22-1 includes a first dispersion generator and cartridge 22-N includes a second dispersion generator. In some example embodiments, and as described further below, at least first and second cartridges 22-1 to 22-N include different dispersion generators configured to generate different dispersions.

Dispersion generators, as described herein, may include different types of dispersion generators configured to generate different types of dispersions. A dispersion may include a vapor, an aerosol or both a vapor and an aerosol. A vapor is a dispersion that is generated through application of heat to a pre-dispersion formulation or through application of mechanical force to a pre-vapor formulation. A pre-dispersion formulation to which heat may be applied to generate a vapor may be referred to as a pre-vapor formulation. An aerosol is a dispersion that is generated through no heating or reduced heating such as sonicating, vibrating or a combination of vibrating and sonicating application to a pre-dispersion formulation. A pre-dispersion formulation to which no heating and/or reduced heating may be applied to generate an aerosol may be referred to as a pre-aerosol formulation.

In some example embodiments, a dispersion generator may be a vaporizer assembly or a nebulizer assembly. A nebulizer assembly may be an atomizer assembly. A vaporizer assembly may generate a dispersion that is a vapor. A vaporizer assembly may generate the vapor via heating a pre-vapor formulation to vaporize at least a portion of the pre-vapor formulation. In an example embodiment, the vaporizer assembly may be a pod.

A nebulizer assembly may generate a dispersion that is an aerosol by non-heating such as by sonication, vibration or a combination of sonication and vibration. For example, a nebulizer assembly may include a vibrator or sonicator rod. In some example embodiments, the nebulizer assembly may be an atomizer assembly that includes a tank holding a pre-aerosol formulation, and the atomizer assembly may further include a mechanical element that includes one or more of a valve, pump, sprayer, some combination thereof, or the like.

One or more portions of the nebulizer assembly, including the vibrator or sonicator rod may exert a force on the pre-aerosol formulation to generate a dispersion that is an aerosol. For example, an atomizer assembly may be configured to generate an aerosol via one or more of releasing a pressurized pre-aerosol formulation into a lower-pressure environment, spraying pre-aerosol formulation particles, evaporating volatile pre-aerosol formulations into an environment, some combination thereof, etc.

Different dispersion generators may include different formulations. For example, the first dispersion generator may be a vaporizer assembly configured to generate a first vapor by heating a pre-vapor formulation and the second dispersion generator may be an atomizer assembly configured to generate a first aerosol by no heating or applying a reduced heat (relative to the heat generated by the vaporizer assembly) to a pre-aerosol formulation.

In some example embodiments, a dispersion generator included in at least one of the cartridges 22-1 to 22-N is configured to generate a dispersion that is substantially free of flavorants. Another dispersion generator included in another at least one of the cartridges 22-1 to 22-N may be configured to generate a separate dispersion that includes one or more flavorants. The separate dispersions generated by the dispersion generators in the separate cartridges 22-1 to 22-N may combine to generate a flavored dispersion.

In some example embodiments, one or more cartridges 22-1 to 22-N may include one or more air inlet ports 45. Air received into an interior of the device 10 via one or more air inlet ports 44 may further be received into an interior of the one or more cartridges 22-1 to 22-N via the one or more air inlet ports 45.

In some example embodiments, one or more cartridges 22-1 to 22-N include one or more openings (not shown in FIG. 1 and FIG. 2) via which one or more of air, dispersions, etc. may exit the one or more cartridges 22-1 to 22-N.

Still referring to FIG. 2, the base 71 includes the cartridge holder 80. The cartridge holder 80, described in further detail below with regard to FIG. 2A, FIG. 2B, and FIG. 2C, includes connectors 33-1 to 33-N and slots 81-1 to 81-N. The cartridge holder 80 is configured to removably couple with one or more cartridges 22-1 to 22-N via connectors 33-1 to 33-N, such that the one or more cartridges 22-1 to 22-N are removably electrically coupled with the power supply 12.

The connectors 33-1 to 33-N are configured to be coupled to separate cartridges 22-1 to 22-N and are further coupled to a connector element 91 of the control circuitry 11 that is discussed further below. As discussed below, the control circuitry 11 is coupled to a power supply 12 in the power supply section 72. Thus, the connectors 33-1 to 33-N may receive power from the control circuitry 11 when the connector element 91 electrically connects the connectors 33-1 to 33-N to the control circuitry 11. Each of connectors 33-1 to 33-N may supply at least a portion of the electrical power from the power supply 12 to a respective coupled one of cartridges 22-1 to 22-N. Each of the connectors 33-1 to 33-N may include at least an anode connector and a cathode connector to supply power to an anode connector and a cathode connector of a respective cartridge 22-1 to 22-N.

The separate slots 81-1 to 81-N may be configured to receive and structurally support separate cartridges 22-1 to 22-N in the device 10. The slots 81-1 to 81-N may be configured to hold separate, respective cartridges 22-1 to 22-N in contact with separate, respective connectors 33-1 to 33-N. In some example embodiments, one or more connectors 33-1 to 33-N are included in one or more slots 81-1 to 81-N. At least one of the slots 81-1 to 81-N may hold at least one of the cartridges 22-1 to 22-N inserted thereto in contact with at least one of the connectors 33-1 to 33-N included in the at least one of the slots 81-1 to 81-N. In some example embodiments, at least one of the slots 81-1 to 81-N is configured to hold an inserted at least one of the cartridges 22-1 to 22-N in contact with at least one of the connectors 33-1 to 33-N via establishing a friction fit or other connection between the at least one of the slots 81-1 to 81-N and the inserted at least one of the cartridges 22-1 to 22-N.

In the example embodiment of FIG. 2, the connectors 33-1 to 33-N are configured to electrically couple the cartridges 22-1 to 22-N inserted into respective slots 81-1 to 81-N with the control circuitry 11 via connector element 91 to provide power to the cartridges 22-1 to 22-N. At least one of the connectors 33-1 to 33-N may be configured to electrically couple at least one dispersion generator included in at least one of the cartridges 22-1 to 22-N with the control circuitry 11. At least one of the connectors 33-1 to 33-N may be directly coupled, connected, etc. to a given dispersion generator included in a given cartridge of cartridges 22-1 to 22-N via directly coupling, connecting, etc. with a connector of the given cartridge of cartridges 22-1 to 22-N.

When the cartridge holder 80 is configured to removably couple with multiple separate cartridges 22-1 to 22-N, the cartridge holder 80 may enable multiple cartridges 22-1 to 22-N to be removably installed in the device 10 at any given time. One or more cartridges 22-1 to 22-N may be individually or collectively added, removed, swapped, replaced, etc. with regard to the base 71 as desired. For example, a given one of cartridges 22-1 to 22-N configured to generate a particular dispersion having a first flavor may be decoupled from one of connectors 33-1 to 33-N and replaced with another one of cartridges 22-1 to 22-N that is configured to generate a different dispersion having a different flavor.

As a result, because the cartridge holder 80 may removably couple with multiple cartridges 22-1 to 22-N, the cartridge holder 80 enables variety and customization of the sensory experience provided during vaping.

In some example embodiments, at least two separate dispersions generated by at least two separate dispersion generators included in separate ones of at least two separate cartridges 22-1 to 22-N may generate separate dispersions that may combine outside of the device 10. In some example embodiments, a device 10, the base 71 or the device 10 and the base 71 is configured to enable manual coupling of various different cartridges 22-1 to 22-N to the cartridge holder 80 to configure the device 10, the base 71 or the device 10 and the base 71 to generate dispersions with various manually-selected combinations of flavors.

In some example embodiments, one or more of the cartridges 22-1 to 22-N may be replaceable and/or refillable. In other words, once one of the formulations of one of the cartridges 22-1 to 22-N is depleted, only the cartridge of cartridges 22-1 to 22-N needs to be replaced or refilled. The cartridges 22-1 to 22-N may be interchangeably coupled with the connectors 33-1 to 33-N. At least one of cartridges 22-1 to 22-N may be swapped for another at least one of the cartridges 22-1 to 22-N. An alternate arrangement may include an example embodiment where the entire device 10 may be disposed once one of the formulations is depleted.

As an example in FIG. 2, the cartridge 22-1 may be replaceable. The cartridge 22-N may be replaceable and refillable. An opening 37 in the outer housing 16 aligns with an opening of the cartridge 22-N to pour a pre-vapor formulation or pre-aerosol formulation into the cartridge 22-N. A removable plug 38 may seal the opening 37 to prevent any leaking external to the outer housing 16.

Still referring to FIG. 1 and FIG. 2, the device 10 includes a cover 70 that may be removably coupled to one or more of the cartridge holder 80 or the power supply section 72 to establish a removable enclosure of cartridges 22-1 to 22-N coupled to the cartridge holder 80. The cover 70 may be configured to establish a removable enclosure of the connectors 33-1 to 33-N, such that the cover 70 may establish a removable enclosure of one or more cartridges 22-1 to 22-N when the one or more cartridges 22-1 to 22-N are coupled to one or more of the connectors 33-1 to 33-N.

The cover 70 includes an outer housing 16, an outlet end insert 20 at an outlet end of the outer housing 16, and an interface 74 at a tip end of the outer housing 16. The outer housing 16 extends in a longitudinal direction. The outer housing 16 may have a generally cylindrical cross-section. In some example embodiments, the outer housing 16 may have a generally triangular cross-section, a generally rectangular cross-section, a generally oval cross-section, a generally square cross-section, a generally polygonal cross-section, or any other suitable cross-section shape along the cover 70. In some example embodiments, the outer housing 16 may have a greater circumference or dimensions at a tip end than at an outlet end of the device 10.

In other example embodiments, the outer housing 16 may have a generally rectangular, oval, square, or polygonal cross-section, or any other suitable cross-section shape along the first section 105, the base 110, or both.

Furthermore, the housings 16 and 17 may have the same or different cross-section shape, or the same or different size.

The outlet end insert 20 is positioned at an outlet end of the cover 70. The outlet end insert 20 includes N outlet ports 21, which may be located on-axis and/or off-axis from the longitudinal axis of the device 10. The outlet ports 21 may be angled outwardly in relation to the longitudinal axis of the device 10. The outlet ports 21 may be distributed about the outlet end insert 20 so as to align with the cartridges 22-1 to 22-N, respectively. Thus, as the dispersion is drawn through the outlet ports 21, the dispersion may move in different directions.

Figure 3:
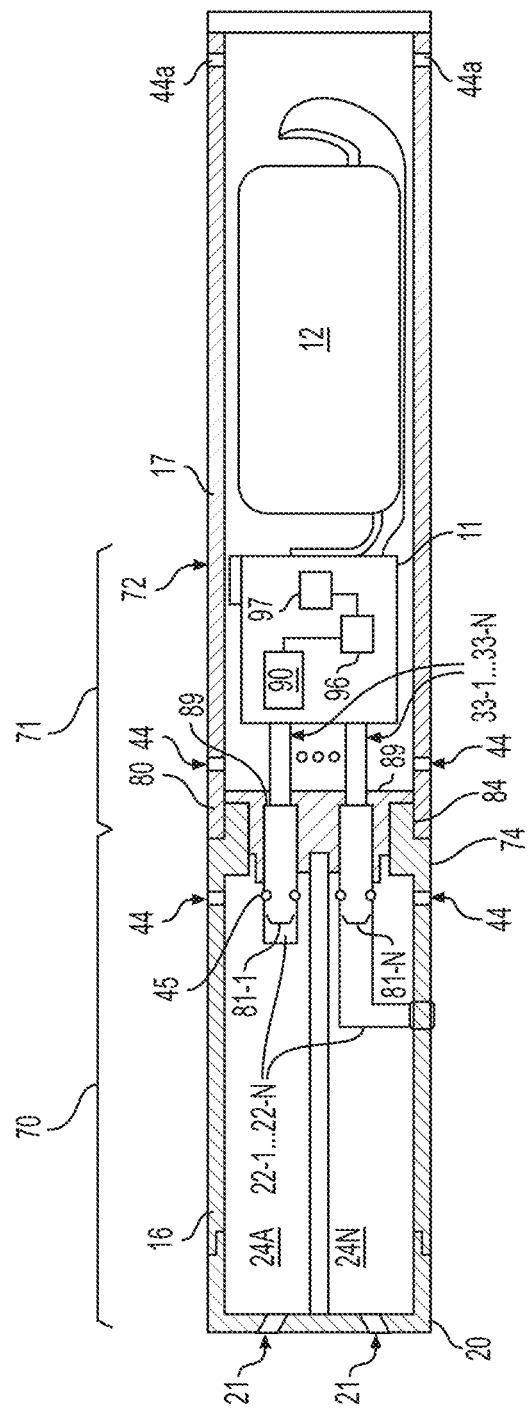

In the embodiment shown in FIG. 2, the cartridges 22-1 to 22-N contact the outlet end insert 20 or have minimal spacing between the cartridges 22-1 to 22-N to prevent and/or reduce particles produced by the dispersion generator in the cartridge 22-1 from mixing with smaller particles generated by the dispersion generator in the cartridge 22-N In an embodiment shown in FIG. 3, the cartridge holder 80 may include a divider 23 configured to partition a portion of the outer housing 16 interior when the cover 70 is coupled to the base 71. In some example embodiments, the divider 23 partitions the connectors 33-1 to 33-N, such that the separate cartridges 22-1 to 22-N coupled to the separate connectors 33-1 to 33-N may generate separate dispersions in isolation from each other. In some example embodiments, the divider 23 is coupled to the outer housing 16 instead of being coupled to the cartridge holder 80, and the divider 23 partitions the connectors 33-1 to 33-N based on the cover 70 being coupled to the base 71. The divider 23 may extend from the cartridge holder to the outlet end insert 20 to prevent and/or reduce dispersions generated by the dispersion generators in the cartridges 22-1 to 22-N from mixing within the device 10. For example, the divider 23 may prevent and/or reduce particles produced by the dispersion generator in the cartridge 22-1 from mixing with smaller particles generated by the dispersion generator in the cartridge 22-N.

The cover 70 may define an enclosure that includes passages 24A to 24N within the outer housing 16 interior. Dispersions generated by the separate dispersion generators included in the separate, respective cartridges 22-1 to 22-N may pass through the passages 24A to 24N to the outlet ports 21 of the outlet end insert 20 to exit the device 10 during vaping. Thus, a dispersions may be generated and emitted as separate dispersions, where the separate dispersions are generated separately by separate dispersion generators included in separate cartridges 22-1 to 22-N.

In some example embodiments, maintaining separate dispersions in the cover 70 mitigates chemical reactions between the separate elements of the separate dispersions. For example, isolating the dispersions in the cover 70 may result in dispersions of different physiochemical properties being provided to an adult vaper.

Referring to FIGS. 1-2, the device 10 includes one or more air inlet ports 44. In the example embodiment shown in FIG. 1 and FIG. 2, air inlet ports 44 are included in both the outer housing 16 of the cover 70 and the outer housing 17 of the base 71. In some example embodiments, the device 10 may include one or more air inlet ports 44 restricted to the outer housing 16 of the cover 70. In some example embodiments, the e-vaping device may include one or more air inlet ports 44 restricted to the outer housing 17 of the base 71.

It should be appreciated that more than two air inlet ports 44 may be included in the outer housing 16, the outer housing 17 or both the outer housing 16 and the outer housing 17. Alternatively, a single air inlet port 44 may be included in the outer housing 16 or the outer housing 17. Such arrangement may also reinforce the area of air inlet ports 44 to facilitate precise drilling of the air inlet ports 44. In some example embodiments, one or more air inlet ports 44 may be provided in the interface 74.

In some example embodiments, at least one air inlet port 44 may be formed in the outer housing 16, adjacent to the interface 74 to minimize the probability of an adult vaper's fingers occluding one of the ports and to control the resistance-to-draw (RTD) during vaping. In some example embodiments, the air inlet ports 44 may be machined into the outer housing 16 with precision tooling such that their diameters are closely controlled and replicated from one device 10 to the next during manufacture.

In some example embodiments, one or more air inlet ports 44 may be drilled with carbide drill bits or other high-precision tools and/or techniques. In yet a further example embodiment, the outer housing 16 may be formed of metal or metal alloys such that the size and shape of the air inlet ports 44 may not be altered during manufacturing operations, packaging, and vaping. Thus, the air inlet ports 44 may provide consistent RTD. In yet a further example embodiment, the air inlet ports 44 may be sized and configured such that the device 10 has a RTD in the range of from about 60 mm $H_2O$ to about 150 mm $H_2O$.

In some example embodiments, the cartridge holder 80 includes one or more air inlet ports 89. The air inlet ports 89 may be configured to establish one or more air passages between an interior of the base 71 and at least one of slots 81-1 to 81-N. In the example embodiment shown in FIG. 2, the cartridge holder 80 includes separate air inlet ports 89 that are each configured to direct air into a separate slot of the slots 81-1 to 81-N. Air drawn into the interior of the base 71 through one or more air inlet ports 44 formed on the outer housing 17 may be drawn into one or more of the slots 81-1 to 81-N through one or more air inlet ports 89 included in the cartridge holder 80.

If and/or when an air inlet port 89 establishes an air passage between the interior of the base 71 and at least one slot 81-1 to 81-N in which at least one cartridge 22-1 to 22-N is located, air drawn through the air inlet port 89 from the interior of the base 71 may be drawn into the at least one of the cartridges 22-1 to 22-N via one or more air inlet ports 45.

Still referring to FIG. 1 and FIG. 2, the power supply section 72 includes a sensor 13 responsive to air drawn into the power supply section 72 via an air inlet port 44a adjacent to a free end or tip end of the device 10 coupled to the control circuitry 11, at least one power supply 12, end cap 48, connector element 91, and control circuitry 11. The sensor 13 may include one or more various types of sensors, including a negative pressure sensor, a button interface sensor, a microelectromechanical system (MEMS) sensor, a sub-combination thereof or a combination thereof. The power supply 12 may include a battery. The battery may be a rechargeable battery.

According to at least one example embodiment, the sensor 13 may include one or more features set forth in U.S. Pat. No. 9,072,321 to Loi Ling Liu and/or U.S. Patent Application Publication No. 2015/0305410 to Loi Ling Liu, the entire contents of each of which are incorporated herein by reference. However, example embodiments should not be limited to this example.

Electrical power may be supplied from the power supply 12 (via the control circuitry 11) to the electrically coupled cartridges 22-1 to 22-N upon the sensor 13 generating a signal indicative of a vaping condition (e.g., the control circuitry 11 detects a signal from the sensor 13 indicating a pressure above a threshold level).

The power supply 12 may be a known power supply such as a Lithium-ion battery or a fuel cell. The device 10 may be usable by an adult vaper until the energy in the power supply 12 is depleted or in the case of a lithium polymer battery, a minimum voltage cut-off level is achieved.

Further, the power supply 12 may be rechargeable and may include circuitry configured to allow the battery to be chargeable by an external charging device and/or solar panels. To recharge the device 10, a Uniform Serial Bus (USB) charger or other suitable charger assembly may be used.

In addition, the at least one air inlet port 44a is located adjacent to the sensor 13, such that the sensor 13 may sense air flow indicative of an adult vaper initiating vaping.

Further, the control circuitry 11 may independently control the supply of electrical power from the power supply 12 to one or more of the cartridges 22-1 to 22-N responsive to the sensor 13. In some example embodiments, the control circuitry 11 may include a manually operable switch for an adult vaper to initiate vaping. A time-period of the electric current supply to a cartridge of cartridges 22-1 to 22-N may be pre-set depending on the amount of dispersion desired to be generated. In some example embodiments, the control circuitry 11 may control the supply of electrical power to a dispersion generator included in a cartridge of cartridges 22-1 to 22-N as long as the sensor 13 detects a pressure drop.

To control the supply of electrical power to at least one of the cartridges 22-1 to 22-N, the control circuitry 11 may execute one or more instances of computer-executable code. The control circuitry 11 may include processing circuitry 96 and a memory 97. The memory may be a computer-readable storage medium storing computer-executable code.

The processing circuitry 96 may include, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be an application-specific integrated circuit (ASIC).

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more of the control circuitry mentioned above. Examples of program code include both machine code produced by a compiler and higher level program code that is executed using an interpreter.

The memory 97 may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data.

In some example embodiments, the control circuitry 11 may independently adjustably control one or more aspects of the electrical power supplied to respective dispersion generators included in one or more of the respective cartridges 22-1 to 22-N via the respective connectors 33-1 to 33-N. In some example embodiments, the control circuitry 11 selectively controls the supply of electrical power to a selected one or more of the cartridges 22-1 to 22-N, such that at least one dispersion generator included in one or more cartridges 22-1 to 22-N does not generate a dispersion. In some example embodiments, the control circuitry 11 controls the supply of electrical power to the cartridges 22-1 to 22-N, so that the dispersion generators included in the separate cartridges 22-1 to 22-N generate separate dispersions at different times. The control circuitry 11 may control the supply of electrical power to control the generation and delivery of dispersions. Such control may include extending the duration of dispersion generation by one or more dispersion generators.

In some example embodiments, the control circuitry 11 may independently control dispersion generation by separate dispersion generators included in separate cartridges 22-1 to 22-N. For example, the control circuitry 11 may independently control the supply of electrical power to the separate cartridges 22-1 to 22-N via independent control of the supply of electrical power to one or more of the respective connectors 33-1 to 33-N.

In some example embodiments, the control circuitry 11 may independently control one or more aspects of electrical power supplied to one or more separate cartridges 22-1 to 22-N to independently control dispersion generation by one or more dispersion generators included in the one or more separate cartridges 22-1 to 22-N. To control dispersion generation by a dispersion generator, the control circuitry 11 may execute one or more instances of computer-executable code. The control circuitry 11 may include a processor and a memory. The memory may be a computer-readable storage medium storing computer-executable code.

In some example embodiments, a dispersion generator included in at least one of the cartridges 22-1 to 22-N is a vaporizer assembly that includes a reservoir, wick, and heater, and another one of the cartridges 22-1 to 22-N. The control circuitry 11 may independently control vapor generation by the vaporizer assembly by controlling the supply of electrical power to the heater of the vaporizer assembly. The reservoir may hold one or more pre-vapor formulations. The wick may be coupled to the reservoir and may draw pre-vapor formulation from the reservoir. The heater may be coupled to the wick and may be configured to heat the drawn pre-vapor formulation to generate a vapor. The vaporizer assembly may include a connector to which the heater may be electrically coupled. Coupling the connector of the vaporizer assembly to at least one of the connectors 33-1 to 33-N may electrically couple the heater to a power supply 12 via the at least one of the connectors 33-1 to 33-N.

In some example embodiments, control circuitry 11 may selectively and independently control the supply of electrical power to separate cartridges to activate the separate dispersion generators included in the separate cartridges 22-1 to 22-N at different times. For example, the control circuitry 11 may activate one dispersion generator included in a cartridge 22-1 prior to activating another dispersion generator included in cartridge 22-N. In another example, the control circuitry 11 may maintain activation of one dispersion generator included in cartridge 22-1 subsequent to ending an activation of another dispersion generator included in cartridge 22-N.

In some example embodiments, the control circuitry 11 may control the supply of electrical power to activate separate dispersion generators included in separate cartridges 22-1 to 22-N at different times, such that separate cartridges 22-1 to 22-N generate separate dispersions during different, at least partially non-overlapping time periods. The control circuitry 11 may control the supply of electrical power to separate cartridges 22-1 to 22-N according to an activation sequence, so that separate dispersions are generated in the device 10 in a particular sequence according to the activation sequence. Generating separate dispersions according to a particular sequence may provide a sequence of dispersions, one or more combined dispersions, etc. during vaping. Such a sequence of dispersions, one or more combined dispersions, etc. may enhance a sensory experience provided by an e-vaping device.

For example, the control circuitry 11 may control the supply of electrical power to cartridges 22-1 to 22-N to activate two separate dispersion generators respectively included in two separate cartridges 22-1 to 22-N in an alternating sequence, where the control circuitry 11 activates alternate dispersion generators in alternate cartridges 22-1 to 22-N according to successive vaping command signals. Successive vaping command signals may be generated by the sensor 13. As a result, the control circuitry 11 may switch between activating separate dispersion generators included in separate cartridges 22-1 to 22-N in an alternating sequence. Such an alternating activation of separate dispersion generators may enhance a sensory experience provided by a device 10 during vaping. For example, by alternating between separate dispersion generators, the control circuitry 11 may mitigate a buildup of heat in any one dispersion generator due to successive vapings, thereby mitigating a risk of overheating of the device 10, heat-induced chemical reactions involving multiple formulations, etc.

In some example embodiments, one or more cartridges 22-1 to 22-N include one or more storage devices (not shown in FIG. 1 and FIG. 2), where the one or more storage devices store information associated with the respective one or more cartridges 22-1 to 22-N in which the one or more storage devices are included. The control circuitry 11 may access the information from the one or more storage devices. The control circuitry 11 may establish a communication link with one or more storage devices of one or more cartridges 22-1 to 22-N based on the one or more cartridges 22-1 to 22-N being electrically coupled to at least a portion of the base 71 via coupling with one or more connectors 33-1 to 33-N. In some example embodiments, electrically coupling a given cartridge of cartridges 22-1 to 22-N with the power supply 12 via coupling the given cartridge of cartridges 22-1 to 22-N to a connector of connectors 33-1 to 33-N includes communicatively coupling the control circuitry 11 with the cartridge of cartridges 22-1 to 22-N via the connector of connectors 33-1 to 33-N.

As discussed further below with reference to FIGS. 5A-5D, the information stored on a storage device of a given cartridge of cartridges 22-1 to 22-N may include information indicating an identity of a dispersion generator included in the given cartridge 22, a dispersion generator "type" of the given dispersion generator (e.g., vaporizer assembly or nebulizer assembly), particular properties of electrical power to supply to the given cartridge of cartridges 22-1 to 22-N to control dispersion generation by the dispersion generator included in the given cartridge 22, properties of one or more formulations held in the dispersion generator in the given cartridge 22, timing control parameters for supplying electrical power to the given cartridge 22, some combination thereof, or the like.

The control circuitry 11 may independently control dispersion generation by one or more of the dispersion generators included in one or more of the cartridges 22-1 to 22-N based on information accessed from one or more storage devices included in the one or more cartridges 22-1 to 22-N by the control circuitry 11. The control circuitry 11 may, for example, control one or more parameters (e.g., voltage, current and time period of electrical power supplied) of electrical power supplied to a cartridge 22, thereby controlling dispersion generation by the dispersion generator included in the given cartridge 22, based on one or more portions of the information associated with one or more of the cartridges 22-1 to 22-N coupled to the base 71. By including control circuitry 11 that is configured to independently control dispersion generation by dispersion generators included in coupled cartridges 22-1 to 22-N based on associated information accessed from storage devices in one or more cartridges 22-1 to 22-N, a base 71 may provide an improved sensory experience.

As described herein, activating a dispersion generator included in a cartridge of cartridges 22-1 to 22-N may include causing the dispersion generator to generate a dispersion. Such activating may include, for example, supplying electrical power to a heater included in the dispersion generator to vaporize a pre-vapor formulation. Such activating may also include supplying electrical power to a sprayer/sonication assembly, valve assembly, etc. included in the dispersion generator to release a pre-dispersion formulation into an external environment.

A flavorant may include a compound or combination of compounds that may provide flavor and/or aroma. In some example embodiments, a flavorant may include one or more volatile flavor substances.

A flavorant may include one or more of a natural flavorant or an artificial ("synthetic") flavorant. In some example embodiments, a flavorant is one or more of tobacco flavor, menthol, wintergreen, peppermint, herb flavors, fruit flavors, nut flavors, liquor flavors, or combinations thereof. In some example embodiments, a flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material.

In some example embodiments, the tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, blends thereof and the like. The tobacco material may be provided in any suitable form, including, but not limited t tobacco lamina, processed tobacco materials, such as volume expanded or puffed tobacco, processed tobacco stems, such as cut-rolled or cut-puffed stems, reconstituted tobacco materials, blends thereof and the like. In some example embodiments, the tobacco material is in the form of a substantially dry tobacco mass.

A formulation, which may include a pre-dispersion formulation, a pre-aerosol formulation or a pre-vapor formulation, is a material or combination of materials that may be transformed into a dispersion. For example, the formulation may be a liquid, solid and/or gel formulation including, but not limited to, water, beads, solvents, active ingredients, ethanol, plant materials including fibers and extracts, natural or artificial flavors, and/or dispersion formers such as glycerin and propylene glycol. The formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

The formulation may include nicotine or may exclude nicotine. The formulation may include one or more tobacco flavors. The formulation may include one or more flavors which are separate from the one or more tobacco flavors.

In some example embodiments, a formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid, or combinations thereof.

In some example embodiments, a dispersion generator may generate a dispersion that is substantially free of one or more materials being in a gas phase. For example, the dispersion may include one or more materials substantially in a particulate phase and substantially not in a gas phase.

Figure 4:
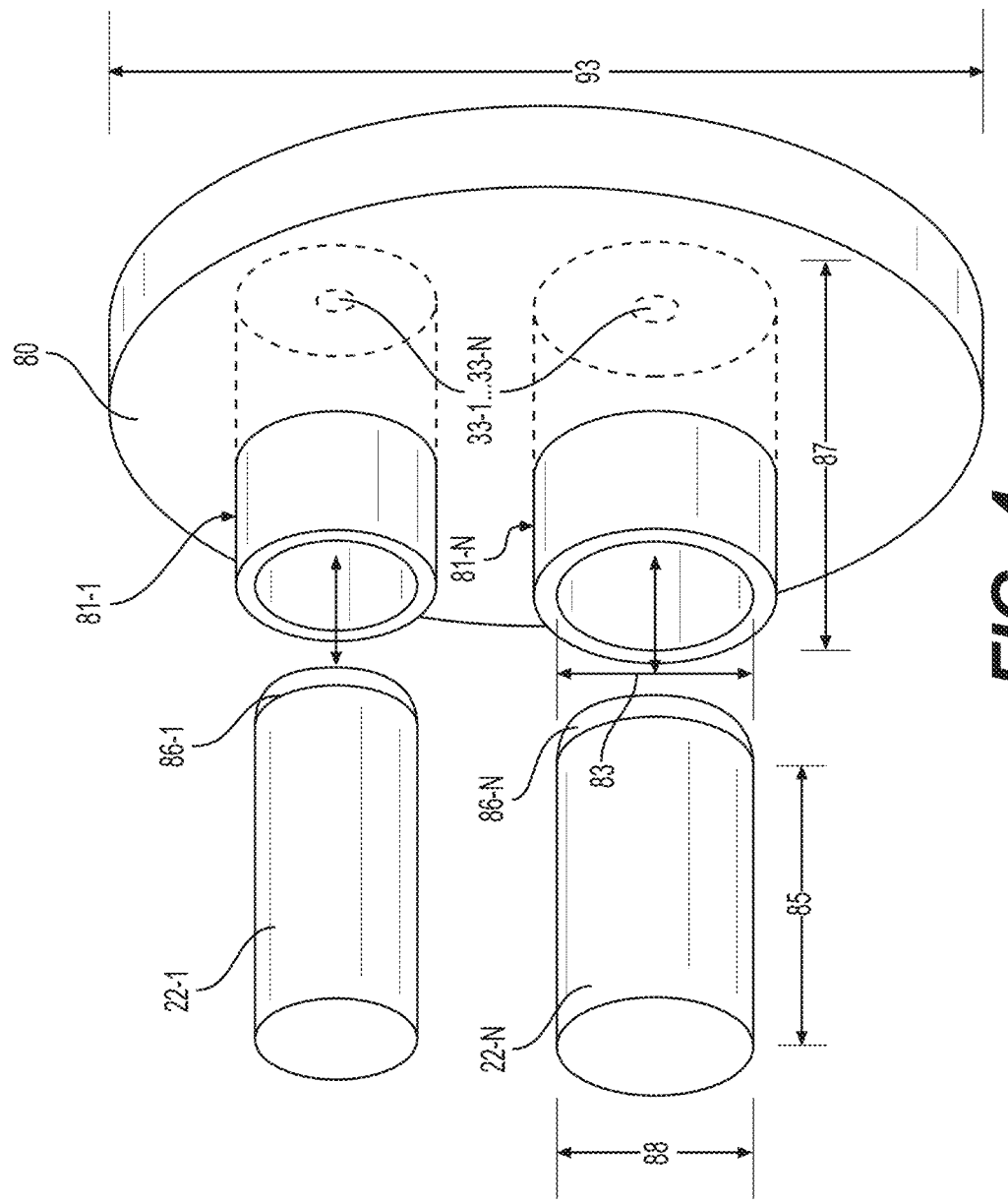

FIG. 4 is a perspective view of a cartridge holder according to some example embodiments. The cartridge holder 80 shown in FIG. 4 may be the cartridge holder 80 included in FIGS. 1-3.

As shown in FIG. 2A, the cartridge holder 80 may include multiple separate slots 81-1 to 81-N. The cartridge holder 80 may have a diameter 93 corresponding to a diameter of the device 10, the base 71 or both the device 10 and the base 71. While the cartridge holder 80 is illustrated as circular, example embodiments are not limited thereto. The cartridge holder 80 may be another shape such as elliptical or rectangular. Each of slots 81-1 to 81-N may extend a length 87. At least part of the length 87 of at least one of the slots 81-1 to 81-N may extend into the cartridge holder 80. The length 87 of at least one of the slots 81-1 to 81-N may be less than a full length 85 of at least one of the cartridges 22-1 to 22-N that the given at least one of the slots 81-1 to 81-N is configured to receive. As a result, at least one of the cartridges 22-1 to 22-N inserted into a given slot of slots 81-1 to 81-N, such that the cartridge of cartridges 22-1 to 22-N completely fills the given slot of slots 81-1 to 81-N and/or may at least partially extend out of the slot of slots 81-1 to 81-N. Each of slots 81-1 to 81-N may have a given diameter 83. The diameter 83 of a given slot of slots 81-1 to 81-N may correspond to an external diameter 88 of at least one of the cartridges 22-1 to 22-N that the given slot of slots 81-1 to 81-N is configured to receive. Different slots 81-1 to 81-N included in the cartridge holder 80 may be configured to receive different cartridges 22-1 to 22-N. Thus, different slots 81-1 to 81-N may have different dimensions, including different diameters 83, lengths 87, shapes, and some combination thereof.

In some example embodiments, a cartridge holder 80 may include at least one of the connectors 33-1 to 33-N that at least partially extends into at least one of the slots 81-1 to 81-N. A portion of a connector of connectors 33-1 to 33-N that extends into a slot of slots 81-1 to 81-N may be referred to herein as a portion of the connector of connectors 33-1 to 33-N that is included in the slot of slots 81-1 to 81-N.

The portion of a given connector of connectors 33-1 to 33-N included in a given slot of slots 81-1 to 81-N may include an electrical interface configured to electrically couple with a connector of at least one of the cartridges 22-1 to 22-N. For example, connector 33-1 included in slot 81-1 may be configured to electrically couple with a connector 86-1 of the given cartridge 22-1. The slot 81-1 may hold the cartridge 22-1 in contact with the connector 33-1.

The portion of a given connector of connectors 33-1 to 33-N included in a given slot of slots 81-1 to 81-N may include a connection interface configured to directly couple, connect, etc. with at least one connector of at least one of the cartridges 22-1 to 22-N. For example, connector 33-1 included may be configured to connect with a connector 86-1 of the given cartridge 22-1 when the cartridge 22-1 is inserted into the slot 81-1. The connector 33-1 may be configured to electrically couple a cartridge 22-1 with a power supply via directly connecting with a connector 86-1 of the cartridge 22-1.

In some example embodiments, a given slot of slots 81-1 to 81-N is configured to accommodate one or more different cartridges 22-1 to 22-N. For example, a slot 81-1 may accommodate a first cartridge of cartridges 22-1 to 22-N that includes a vaporizer assembly, and the slot 81-1 may alternatively accommodate a second cartridge of cartridges 22-1 to 22-N that includes a nebulizer assembly. The first and second cartridges 22-1 to 22-N may be interchangeably swapped from the slot 81-1. For example, the first and second cartridges 22-1 to 22-N may each have a connector 86-1 configured to connect with the connector 33-1 coupled to the given slot 81-1.

Because different cartridges 22-1 to 22-N may be interchangeably installed, removed, etc. from one or more of the slots 81-1 to 81-N, and because different cartridges 22-1 to 22-N may include different dispersion generators, the device 10 may be configured to generate various combined dispersions as desired by an adult vaper. The adult vaper may install selected cartridges 22-1 to 22-N in one or more of the slots 81-1 to 81-N, swap a cartridge of cartridges 22-1 to 22-N in a slot of slots 81-1 to 81-N for a different cartridge of cartridges 22-1 to 22-N as desired, etc. As a result, the adult vaper may customize the combined dispersion provided by the e-vaping device, thereby customizing the sensory experience provided by the device 10. Furthermore, the device 10 enables the combined dispersion to be generated with mitigated risk of chemical reactions between the separate dispersions that combine to generate the combined dispersion.

Because the cartridge holder 80 may include different connectors 33-1 to 33-N configured to couple with different sets of cartridges 22-1 to 22-N, the cartridge holder 80 may enable different types of dispersion generators (e.g., vaporizer assemblies, nebulizer assemblies, etc.) included in different cartridges 22-1 to 22-N to be included in a common the device 10, the base 71 or both the device 10 and the base 71. In addition, the cartridge holder may enable different cartridges including different dispersion generators, even dispersion generators of a common type, to be included in a common device 10, a base 71 or both the device 10 and the based 71 even through the different dispersion generators may have different connectors, dimensions, etc.

As an example, connectors 33-1 and 86-1 may be complementary bayonet connector elements, and connector 86-N may be a threaded connector, such that connector 33-1 is restricted from coupling with connector 86-N.

Connector 33-N is configured to couple with connector 86-N of cartridge 22-N and is restricted from coupling with connector 86-1 of cartridge 22-1. For example, connectors 33-N and 86-N may be complementary threaded connector elements, and connector 86-1 may be a bayonet connector, such that connector 33-N is restricted from coupling with connector 86-1.

In some example embodiments, a cartridge holder 80 may couple with a cartridge 22-1 via a connector 33-N that is restricted from being directly coupled with a connector 86-1 of the cartridge 22-1. An adapter may enable such coupling.

As a result, the adapter and the cartridge holder 80 may enable a dispersion generator to be coupled to the connector, where the dispersion generator would otherwise be restricted from being coupled to a connector of the cartridge holder.

FIG. 5A is a cartridge 22 that includes a dispersion generator 300A according to some example embodiments. FIG. 5B is a cartridge 22 that includes a dispersion generator 300B according to some example embodiments. FIG. 5C is a cartridge 22 that includes a dispersion generator 300C according to some example embodiments. FIG. 5D is a cartridge 22 that includes a dispersion generator 300D according to some example embodiments. Each of the cartridges 22 shown in FIGS. 5A-5D may be included in any and all embodiments of cartridges included herein, including one or more of the cartridges 22-1 to 22-N shown in FIGS. 2-3.

FIG. 5A illustrates a cartridge 22 that includes a dispersion generator 300A that is a vaporizer assembly, according to some example embodiments. As shown in FIG. 5A, the dispersion generator 300A may include a reservoir 309 for a pre-vapor formulation, a wick 308 that is configured to draw the pre-vapor formulation from the reservoir 309, and a heater 306 that may heat the drawn pre-vapor formulation to vaporize the pre-vapor formulation and generate a vapor.

The cartridge 22 may include an outer housing 301 extending in a longitudinal direction and an inner tube 312 coaxially positioned within the outer housing 301. The outer housing 301 may have a generally cylindrical cross-section. In some example embodiments, the outer housing 301 may have a generally triangular cross-section. In some example embodiments, the outer housing 301 may have a greater circumference or dimensions at a tip end than at an outlet end of the cartridge 22.

The cartridge 22 may include a connector 86 at a tip end. The connector 86 may be configured to physically couple with an interface included in one or more sections of the device the base 71 or both the device 10 and the base 71. In some example embodiments, the connector 86 includes an electrical interface. The electrical interface may be configured to electrically couple one or more portions of the cartridge 22 to the control circuitry 11 based on the connector 86 coupling with a portion of one or more sections of the device 10, the base 71 or both the device 10 and the device 71, including the power supply section 72. In the illustrated embodiment, for example, heater 306 is electrically coupled to connector 86 via electrical leads 307. The heater 306 may be supplied with electrical power from a power supply to which the connector 86 and electrical leads 307 electrically couple the heater 306.

At one end of the inner tube 312, a nose portion of a gasket (or seal) 317 may be fitted into an end portion of the inner tube 312, while an outer perimeter of the gasket 317 may provide a substantially tight seal with an interior surface of the outer housing 301. The gasket 317 may also include a central, longitudinal channel 318, which opens into an interior of the inner tube 312 that defines a central channel 320. A space 321 at a backside portion of the gasket 317 may intersect and communicate with the central channel 318 of the gasket 317. This space 321 assures communication between the central channel 318 and one or more air inlet ports 45.

In some example embodiments, a nose portion of another gasket 315 may be fitted into another end portion of the inner tube 312. An outer perimeter of the gasket 315 may provide a substantially tight seal with an interior surface of the outer housing 301. The gasket 315 may include a central channel 316 disposed between the central channel 320 of the inner tube 312 and an opening 303 at an outlet end of the outer housing 301. The central channel 316 may transport a vapor from the central channel 320 to the opening 303 to exit the dispersion generator 300A.

The space defined between the gaskets 315 and 317 and the outer housing 301 and the inner tube 312 may establish the confines of the reservoir 309. The reservoir 309 may include a pre-vapor formulation, and optionally a storage medium configured to store the pre-vapor formulation therein. The storage medium may include a winding of cotton gauze or other fibrous material about a portion of the dispersion generator 300A. The reservoir 309 may be contained in an outer annulus between the inner tube 312 and the outer housing 301 and between the gaskets 315 and 317. Thus, the reservoir 309 may at least partially surround the central channel 320. The heater 306 may extend transversely across the central channel 320 between opposing portions of the reservoir 309. In some example embodiments, the heater 306 may extend parallel to a longitudinal axis of the central channel 320.

The dispersion generator 300A may include a wick 308 configured to draw pre-vapor formulation from the reservoir 309, such that the pre-vapor formulation may be vaporized from the wick 308 based on heating of the wick 308 by the heater 306. During vaping, pre-vapor formulation may be transferred from the reservoir 309 and/or storage medium in the proximity of the heater 306 via capillary action of the wick 308. The wick 308 may include a first end portion and a second end portion, which may extend into opposite sides of the reservoir 309. Wick end portions may be referred to herein as wick roots. The heater 306 may at least partially surround a central portion of the wick such that when the heater 306 is activated, the pre-vapor formulation in the central portion of the wick 308 may be vaporized by the heater 306 to generate a vapor. The central portion of a wick may be referred to herein as a wick trunk.

The wick 308 may include filaments (or threads) having a capacity to draw the pre-vapor formulation.

In some example embodiments, the heater 306 may include a wire coil which at least partially surrounds the wick 308 in the dispersion generator 300A. The wire may be a metal wire and/or the wire coil may extend fully or partially along the length of the wick. The wire coil may further extend fully or partially around the circumference of the wick. In some example embodiments, the wire coil may or may not be in contact with the wick.

The wire coil may be formed of any suitable electrically resistive materials. The heater 306 may include at least one material selected from the group consisting of stainless steel, copper, copper alloys, nickel-chromium alloys, super alloys and combinations thereof. In an example embodiment, the heater 306 may be formed of nickel-chromium alloys or iron-chromium alloys. In another example embodiment, the heater 306 may be a ceramic heater having an electrically resistive layer on an outside surface thereof.

It should be appreciated that, instead of using a wick, the heater 306 may be a porous material which incorporates a resistance heater formed of a material having a high electrical resistance capable of generating heat quickly.

The cartridge 22 may include an opening 303 in the outer housing 301. A vapor generated by the heater 306 of the dispersion generator 300A may be directed out of the dispersion generator 300A through the central channel 316 and the opening 303 to exit the cartridge 22.

In some example embodiments, a cartridge 22 includes one or more storage devices 390. A storage device 390 may be configured to be electrically, communicatively coupled to connector 86. The storage device 390 may include information associated with the dispersion generator 300 included in the cartridge 22 in which the storage device 390 is included. Such information may be referred to as "cartridge information," where the cartridge information stored in a storage device 390 of a given cartridge 22 includes information associated with the dispersion generator included in the given cartridge. The cartridge information associated with the dispersion generator 300 may include information uniquely identifying one or more elements of the dispersion generator, including the dispersion generator 300 itself, a formulation held by the dispersion generator 300, information indicating a dispersion generator "type" of the given dispersion generator 300 (e.g., vaporizer assembly or nebulizer assembly), or some combination thereof. Formulation information may include information indicating a flavor associated with a dispersion generated by the given dispersion generator 300, viscosity information associated with the formulation, etc. The information may indicate one or more parameters of electrical power to be supplied to the dispersion generator 300 via connector 86 during vaping, including one or more of a particular voltage, current, time period during which to supply the electrical power, etc. The information may indicate a particular sequence according to which the dispersion generator is to be activated.

The cartridge information associated with the dispersion generator 300, stored in the storage device 390, may be accessed via connector 86 by the control circuitry 11 to which the given dispersion generator 300 may be coupled through connector 86. The control circuitry 11 may independently control dispersion generation by one or more dispersion generators 300 based on the accessed cartridge information.

As shown in FIG. 5B, a dispersion generator 300B included in a cartridge 22 may be an atomizer assembly that includes a pre-aerosol formulation emitter 330 configured to release a pre-aerosol formulation into an external environment to generate an aerosol. The emitter 330 may be one or more of a fluid sprayer, compressed gas emitter, vibrator, sonicator, etc. As shown, the emitter 330 includes a reservoir housing 331 in which a pre-aerosol formulation 332 is held. In some example embodiments, the reservoir housing 331 is at least partially incorporated into the outer housing 301 of the cartridge 22.

In some example embodiments, the emitter 330 holds a pre-aerosol formulation at an elevated pressure, relative to an external environment of the emitter 330. For example, the pre-aerosol formulation may be a pressurized gas.

The emitter 330 includes a dispensing interface 334 configured to release the pre-aerosol formulation 332 into the external environment through opening 303. The dispensing interface 334 may be electrically coupled to connector 86 via one or more electrical leads 307, such that one or more portions of the dispensing interface 334 may be selectively controlled to release a pre-aerosol formulation.

The dispensing interface includes a channel 336 and a dispensing control element 335. The dispensing control element 335 controls a release of the pre-aerosol formulation into the external environment via channel 336. In some example embodiments, the dispensing control element 335 is a valve assembly. A valve assembly may be controlled to release pre-aerosol formulation based on a supply of electrical power to the valve assembly via electrical leads 307.

For example, where the emitter 330 is a pressurized gas emitter, the dispensing control element 335 may be a valve assembly configured to selectively release pressurized gas to generate an aerosol. In some example embodiments, the pre-aerosol formulation 332 is held in the reservoir housing 331 in a phase that is separate from a pure gas phase and at an elevated pressure, and the emitter 330 is configured to generate an aerosol based on a pressure differential across the dispensing control element 335 that includes a valve assembly as the pre-aerosol formulation passes through the channel 336 to the external environment.

In another example, where the emitter 330 is a fluid sprayer, the dispensing control element 335 may be a sprayer assembly configured to spray a fluid pre-aerosol formulation 332 into the external environment to generate an aerosol. In some example embodiments, the sprayer assembly includes a pump device.

In some example embodiments, the pre-aerosol formulation 332 includes a volatile substance, and the volatile substance may vaporize to generate an aerosol when the pre-aerosol formulation 332 is released into an external environment by the dispensing interface 334.

As shown in FIG. 5C, a dispersion generator 300C included in a cartridge 22 may be a nebulizer assembly that includes a rod 350 configured to generate aerosol from the pre-aerosol formulation 332. In some example embodiments, the rod 350 is a sonicator that generates ultrasonic waves to cause at least some of the pre-aerosol formulation 332 to transform into an aerosol at a surface of a mesh plate 352. In other example embodiments, the rod 350 is a vibrate that generates a vibrating movement at the mesh plate 352 and cause at least some of the pre-aerosol formulation 332 to transform into an aerosol at the mesh plate 352.

As shown, the dispersion generator 300C includes the outer housing 301 and the mesh plate 352. The mesh plate 352 traverses an opening in the outer housing 301 to contain the pre-aerosol formulation 332 in the outer housing 301 and prevent and/or reduce the pre-aerosol formulation 332 from leaking out of the outer housing 301. The mesh plate 352 and the outer housing 301 define an internal volume 356 to contain the pre-aerosol formulation 332. In some example embodiments, the reservoir housing 331 is at least partially incorporated into the outer housing 301 of the cartridge 22.

The mesh plate 352 includes holes 354 that are sized to allow an aerosol to flow from the internal volume 356 to the opening 303. In some example embodiments, the holes 354 may have a diameter between 4-6 microns.

The rod 350 is configured to release the pre-aerosol formulation 332 into the external environment through opening 303 (e.g., by vibration or sonication). The air inlet port 45 permits the aerosol to air flow to the opening 303. The rod 350 may be electrically coupled to the connector 86 via one or more electrical leads 307, such that the rod 350 may be selectively controlled to release a pre-aerosol formulation.

The rod 350 and the mesh plate 352 controls a release of the pre-aerosol formulation into the external environment via a channel 336.

In some example embodiments, the pre-aerosol formulation 332 is held in the outer housing 301 in a liquid or solid phase.

In some example embodiments, the pre-aerosol formulation 332 includes a volatile substance, and the volatile substance may transform to an aerosol when the rod 350 vibrates the pre-aerosol formulation 332.

An opening 370 in the dispersion generator 300C aligns with the opening 37 (shown in FIGS. 2-3) to pour a pre-vapor formulation or pre-aerosol formulation into the dispersion generator 300C. The removable plug 38 (shown in FIGS. 2-3) may seal the opening 370 and the cartridge 22 to prevent and/or reduce any leaking from the internal volume 356 to outside the outer housing 16.

FIG. 5D illustrates a dispersion generator 300D included in the cartridge 22 may be a nebulizer assembly that includes a plate 391. In some example embodiments, the plate 391 is a vibrator. In other example embodiments, the plate 391 is a sonicator. As shown in FIG. 5D, the dispersion generator 300D may include a reservoir 309A for a pre-vapor formulation and the plate 391 that may vibrate the pre-vapor formulation to transform at least a portion of the pre-vapor formulation to generate an aerosol.

The cartridge 22 may include the outer housing 301 and an inner tube 312A coaxially positioned within the outer housing 301.

In the illustrated embodiment, for example, the plate 391 is electrically coupled to the connector 86 via the electrical leads 307. The plate 391 may be supplied with electrical power from a power supply to which the connector 86 and the electrical leads 307 electrically couple the plate 391.

The reservoir 309A may include a pre-vapor formulation, and optionally a storage medium configured to store the pre-vapor formulation therein. The storage medium may include a winding of cotton gauze or other fibrous material about a portion of the dispersion generator 300D. The reservoir 309A may be contained in an outer annulus between the inner tube 312A and the outer housing 301. Thus, the reservoir 309A may at least partially surround a central channel 320A.

The central channel 320A is positioned between the channel 358 and the vibrator plate 391. The plate 391 may extend transversely across an end of the central channel 320A between opposing portions of the outer housing 301. In some example embodiments, the plate 391 may extend parallel to a longitudinal axis of the central channel 320A.

In some example embodiments, the inner tube 312A may be omitted and the central channel 320A may not extend through the reservoir 309A.

During aerosol generation, at least a portion of the pre-vapor formulation may be transformed into an aerosol by the vibrations or ultrasonic waves caused by the plate 391, in some example embodiments.

In some example embodiments, the reservoir 309A may be removed through the opening 303 and replaced with a new reservoir.

FIGS. 6A-6D illustrate example embodiments of the outlet end insert 20.

Figure 6A:
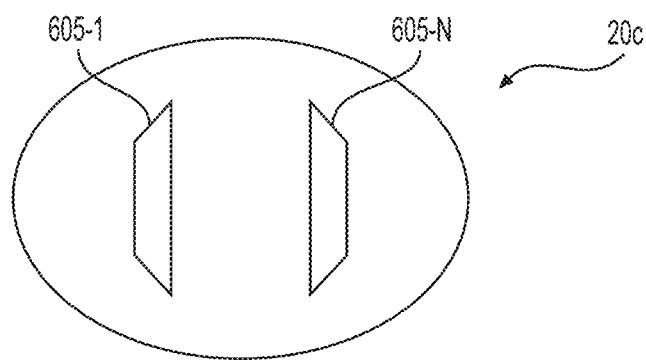

FIG. 6A illustrates an outlet end insert 20a. In some example embodiments, the outlet end insert 20a is circular and has N outlets 605-1 to 605-N for N dispersion generators. Each of the outlets 605-1 to 605-N is associated with one of the N dispersion generators such that the dispersions generated by the dispersion generators do not mix within the device 10. As shown in FIG. 6A, the outlets 605-1 to 605-N are trapezoid shaped, however, the outlets 605-1 to 605-N are not limited thereto. For example, in other example embodiments, the outlets 605-1 to 605-N may be circular or shaped. Moreover, at least two of the outlets 605-1 to 605-N may have a different shape.

Figure 6B:
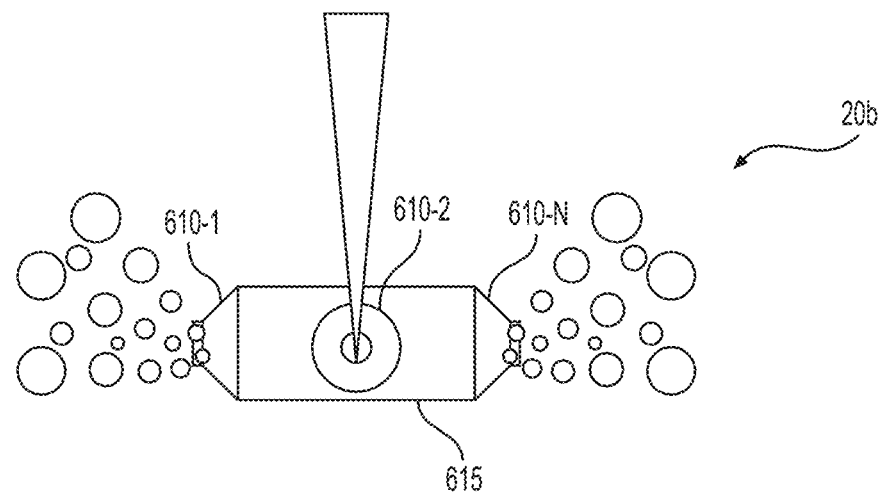

FIG. 6B illustrates an outlet end insert 20b. In some example embodiments, the outlet end insert 20b includes outlets 610-1 to 610-N. Each of the outlets 610-1 to 610-N is designed for and corresponds to a particular type of dispersion. For example, the outlets 610-1 and 610-N are trapezoid shaped and designed for a vapor generator.

Figure 6C:
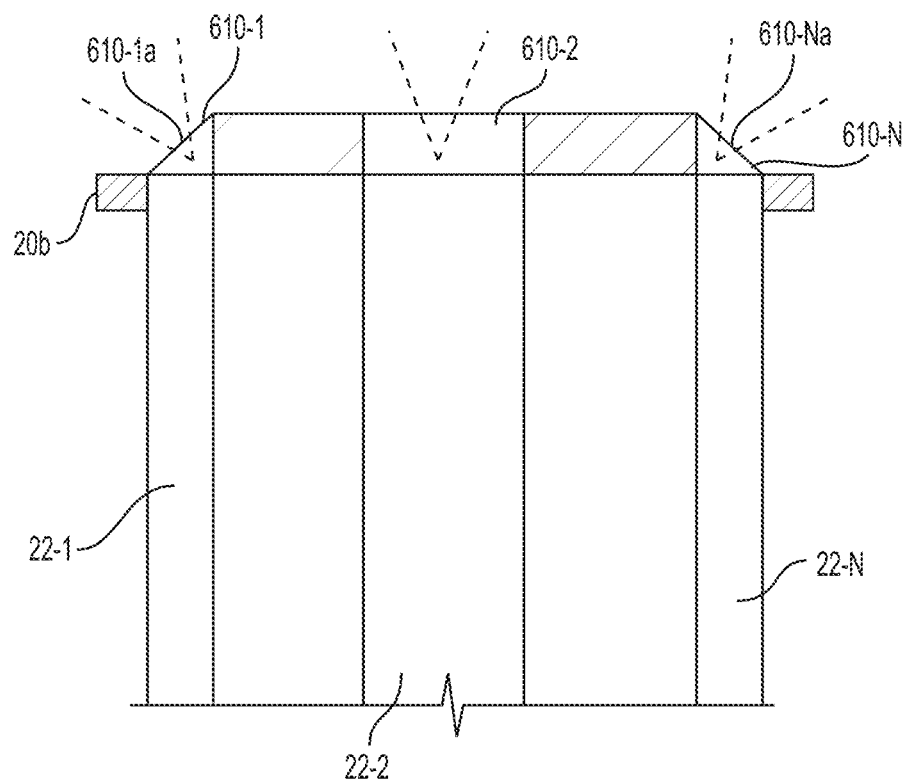

Moreover, in some example embodiments, the outlets 610-1 and 610-N are at edges of a base 615 of the outlet end insert 20b. As shown in FIG. 6C, the outlets 610-1 and 610-N are angled to allow a dispersion in a partial sidewise fashion. The outlets 610-1 and 610-N have triangular cross sections and the dispersions exit the outlet end insert 20b at respective hypotenuse sides 610-1a and 610-Na.

The outlet 610-2 may be circular and designed for an aerosol generator. The outlet 610-2 may be between the outlets 610-1 and 610-N. Because each of the outlets 610-1 to 610-N is associated with one of the N dispersion generators and are for a particular type of dispersion, an aerosol and a vapor exit the outlet end insert 20b when the device 10 is in use. For example, the aerosol exiting the outlets 610-1 and 610-N may have a mass median aerodynamic diameter (MMAD) of 4-6 µm and the vapor exiting the outlet 610-2 may have a MMD of 0.5-1 µm. In some example embodiments, the outlets 610-1 to 610-N are aligned with the N dispersion generators, respectively.

Figure 6D:
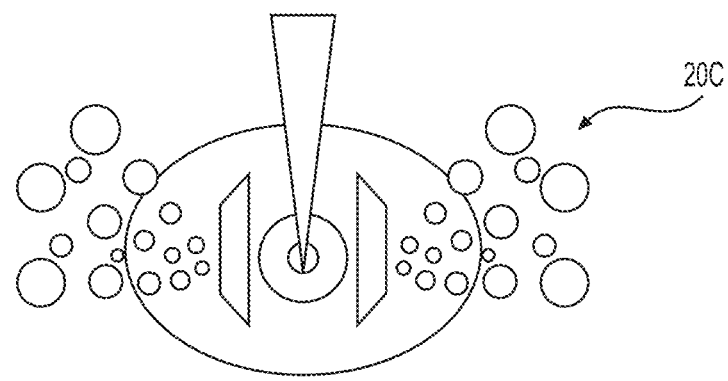

FIG. 6D illustrates an outlet end insert 20c. The outlet end insert 20c may be the same as the outlet end insert 20a except the outlet end insert 20c includes the outlet 610-2.

FIGS. 7A-7B an outlet end insert according to some example embodiments.

FIG. 7A illustrates a top view of an outlet end insert 20d. In some example embodiments, the outlet end insert 20d includes outlets 710-1 to 710-N. Each of the outlets 710-1 to 710-N is designed for and corresponds to a particular type of dispersion. For example, the outlet 710-1 may be for a vapor generator and the outlet 710-N may designed for an aerosol generator. In some example embodiments, the outlets 710-1 and 710-N are trapezoid shaped.

Moreover, in some example embodiments, the outlets 710-1 and 710-N are at edges of a base 715 of the outlet end insert 20b.

FIG. 7B illustrates a cross sectional view of the outlet end insert 20d. As shown in FIG. 7B, the outlets 710-1 and 710-N are angled to allow a dispersion in a partial sidewise fashion. The outlets 710-1 and 710-N have triangular cross sections and the dispersions exit the outlet end insert 20d at respective hypotenuse sides 710-1a and 710-Na.

As shown, the divider 23 abuts the outlet end insert 20d to prevent a dispersion in the passage 24A from mixing with the dispersion in the passage 24N. Consequently, the dispersion in the passage 24A and the dispersion in the passage 24N exit the outlet end insert 20d as separate dispersions upon a negative pressure being applied on the passages 24A and 24N.

Because each of the outlets 710-1 to 710-N is associated with one of the N dispersion generators and are for a particular type of dispersion, an aerosol and a vapor exit the outlet end insert 20d when the device 10 is in use. For example, the aerosol exiting the outlet 710-N may have a mass median aerodynamic diameter (MMAD) of 4-6 µm and the vapor exiting the outlet 710-1 may have a MMD of 0.5-1 µm. In some example embodiments, the outlets 610-1 to 610-N are aligned with the N dispersion generators, respectively.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A dispersion device comprising:
   a cover including,
      an outer housing having a first end and a second end,
      at least two cartridges within the outer housing and extending from the first end to the second end, and
      an outlet end element at the first end of the outer housing, the at least two cartridges contacting the outlet end element such that outlets of each of the at least two cartridges are isolated; and
   a base configured to be coupled to the cover adjacent the second end of the outer housing, the base including,
      a cartridge holder configured to receive the at least two cartridges, and
      a power supply.

2. The dispersion device of claim 1, wherein the at least two cartridges includes,
   a first cartridge containing a first pre-vapor formulation; and a second cartridge containing a first pre-aerosol formulation, the first pre-vapor formulation and the first pre-aerosol formulation being different.

3. The dispersion device of claim 1, wherein the at least two cartridges includes,
a first cartridge including a first dispersion generating system; and
a second cartridge including a second dispersion generating system.

4. The dispersion device of claim 3, wherein:
the first dispersion generating system is configured to vaporize a first pre-vapor formulation into a first vapor having particles of a first size; and
the second dispersion generating system is configured to aerosolize a first pre-aerosol formulation into a first aerosol having particles of a second size and the first size and the second size are different.

5. The dispersion device of claim 4, wherein the first dispersion generating system includes a heater and the second dispersion generating system includes a heatless vapor generator.

6. The dispersion device of claim 4, wherein the first dispersion generating system includes a heater configured to generate the first vapor and the second dispersion generating system includes an ultra-sonic generator or a vibrator configured to generate the first aerosol.

7. The dispersion device of claim 1, wherein the outlet end element comprises:
a first outlet corresponding to a first cartridge of the at least two cartridges; and
a second outlet corresponding to a second cartridge of the at least two cartridges, the second outlet being separate from the first outlet.

8. The dispersion device of claim 7, wherein:
the first outlet is at a center of the outlet end element; and
the second outlet includes first and second parts at end portions of the outlet end element.

9. The dispersion device of claim 7, further comprising:
a divider separating the first cartridge and the first outlet from the second cartridge and the second outlet.

10. The dispersion device of claim 7, wherein the first outlet and the second outlet are angled with respect to a longitudinal axis of the dispersion device.

11. The dispersion device of claim 1, wherein:
the power supply is configured to be coupled to the at least two cartridges.

12. The dispersion device of claim 1, further comprising:
a divider defining first and second passages in the outer housing, a first cartridge of the at least two cartridges being in the first passage and a second cartridge of the at least two cartridges being in the second passage.

13. The dispersion device of claim 12, wherein the divider extends to the outlet end element and separates a first outlet in the outlet end element and a second outlet in the outlet end element.

14. The dispersion device of claim 12, wherein the outer housing defines a first opening through a surface of the outer housing, the first cartridge defines a second opening, and the first opening and the second opening align.

15. The dispersion device of claim 1, wherein the at least two cartridges include,
a sonicator configured to exert a force on a pre-aerosol formulation, and
a mesh plate adjacent to the pre-aerosol formulation, the mesh plate defining holes such that an aerosol exits the mesh plate when the sonicator exerts the force on the pre-aerosol formulation, the mesh plate separates the pre-aerosol formulation from a channel.

16. The dispersion device of claim 1, wherein the at least two cartridges include,
a pre-aerosol formulation reservoir configured to contain a pre-aerosol formulation,
an inner tube defining a central channel through the pre-aerosol formulation reservoir, and
a vibrator configured to vibrate the pre-aerosol formulation to generate a vapor.

17. The dispersion device of claim 16, wherein the vibrator is a plate and contacts the pre-aerosol formulation reservoir.

18. The dispersion device of claim 17, wherein the inner tube extends from the plate to an end of the pre-aerosol formulation reservoir.

19. The dispersion device of claim 1, wherein each of the at least two cartridges include an air inlet.

20. The dispersion device of claim 1, wherein the cartridge holder includes,
a first slot configured to receive a first cartridge of the at least two cartridges, and
a second slot configured to receive a second cartridge of the at least two cartridges.

* * * * *